(12) United States Patent
Ren et al.

(10) Patent No.: US 12,268,390 B2
(45) Date of Patent: Apr. 8, 2025

(54) STAPLING DEVICE WITH REPLACEABLE CARTRIDGE MODULE

(71) Applicant: Covidien LP, Mansfield, MA (US)

(72) Inventors: Ping Ren, Shanghai (CN); Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/290,636

(22) PCT Filed: Jul. 19, 2021

(86) PCT No.: PCT/CN2021/107036
§ 371 (c)(1),
(2) Date: Jan. 19, 2024

(87) PCT Pub. No.: WO2023/000127
PCT Pub. Date: Jan. 26, 2023

(65) Prior Publication Data
US 2024/0335195 A1 Oct. 10, 2024

(51) Int. Cl.
*A61B 17/072* (2006.01)
*A61B 17/00* (2006.01)

(52) U.S. Cl.
CPC .. *A61B 17/072* (2013.01); *A61B 2017/00477* (2013.01); *A61B 2017/07221* (2013.01); *A61B 2017/07257* (2013.01); *A61B 2017/07271* (2013.01)

(58) Field of Classification Search
CPC .................................................. A61B 17/072
See application file for complete search history.

(56) References Cited

U.S. PATENT DOCUMENTS

| | | | |
|---|---|---|---|
| 1,158,111 | A | 10/1915 | Ahlheim |
| 2,891,250 | A | 6/1959 | Hirata |
| 3,080,564 | A | 3/1963 | Strekopitov et al. |
| 3,252,643 | A | 5/1966 | Strekopov et al. |
| 3,269,630 | A | 8/1966 | Fleischer |
| 3,275,211 | A | 9/1966 | Hirsch et al. |
| 3,315,863 | A | 4/1967 | O'Dea |
| 3,494,533 | A | 2/1970 | Green et al. |
| 3,589,589 | A | 6/1971 | Akopov |

(Continued)

FOREIGN PATENT DOCUMENTS

| CN | 1669534 A | 9/2005 |
|---|---|---|
| CN | 202619749 U | 12/2012 |

(Continued)

OTHER PUBLICATIONS

International Search Report for Application No. PCT/CN2021/107036 dated Apr. 19, 2022.

(Continued)

*Primary Examiner* — Nathaniel C Chukwurah (57) ABSTRACT

A surgical stapling device includes a clamp slide assembly and an end effector that includes a cartridge module. The clamp slide assembly includes a distal portion that defines a curved slot and includes a linear section that defines linear channels. The cartridge module includes a curved module body that includes a linear section that includes linear ribs. The linear ribs are received within the linear channels to facilitate loading of the cartridge module into the distal portion of the clamp slide assembly in a linear fashion.

20 Claims, 7 Drawing Sheets

(56) References Cited

U.S. PATENT DOCUMENTS

| | | |
|---|---|---|
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,571,285 A | 11/1996 | Chow et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,828,188 B2 | 11/2010 | Jankowski |
| 7,886,953 B2 | 2/2011 | Schwemberger et al. |
| 8,016,176 B2 | 9/2011 | Kasvikis et al. |
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,328,064 B2 | 12/2012 | Racenet et al. |
| 8,360,296 B2 | 1/2013 | Zingman |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |

(56) References Cited

U.S. PATENT DOCUMENTS

| | | |
|---|---|---|
| 8,757,467 B2 | 6/2014 | Racenet et al. |
| 8,936,185 B2 | 1/2015 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 * | 9/2015 | Mandakolathur Vasudevan ......... A61B 17/072 |
| 9,192,382 B2 | 11/2015 | Kostrzewski |
| 9,192,387 B1 | 11/2015 | Holsten et al. |
| 9,480,474 B2 | 11/2016 | Ji et al. |
| 9,566,066 B2 | 2/2017 | Kasvikis |
| 9,579,102 B2 | 2/2017 | Holsten et al. |
| 9,655,619 B2 | 5/2017 | Zhang et al. |
| 9,662,111 B2 | 5/2017 | Holsten et al. |
| 9,668,736 B2 | 6/2017 | Holsten et al. |
| 9,675,349 B2 | 6/2017 | Holsten et al. |
| 9,675,350 B2 | 6/2017 | Holsten et al. |
| 9,675,356 B2 | 6/2017 | Racenet et al. |
| 9,814,460 B2 | 11/2017 | Kimsey et al. |
| 9,888,923 B2 | 2/2018 | Chen et al. |
| 9,962,159 B2 | 5/2018 | Heinrich et al. |
| 10,004,504 B2 | 6/2018 | Bryant |
| 10,085,754 B2 | 10/2018 | Sniffin et al. |
| 10,194,913 B2 | 2/2019 | Nalagatla et al. |
| 2004/0164123 A1 | 8/2004 | Racenet et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0187456 A1 | 8/2007 | Viola et al. |
| 2010/0048988 A1 | 2/2010 | Pastorelli et al. |
| 2013/0206813 A1 | 8/2013 | Nalagatla |
| 2016/0249914 A1 | 9/2016 | Zhang et al. |
| 2016/0249923 A1 | 9/2016 | Hodgkinson et al. |
| 2016/0270784 A1 | 9/2016 | Wheeler et al. |
| 2016/0270790 A1 | 9/2016 | Jankowski |
| 2016/0270793 A1 | 9/2016 | Carter et al. |
| 2016/0278779 A1 | 9/2016 | Jankowski |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0128149 A1 | 5/2017 | Heinrich et al. |
| 2017/0238923 A1 | 8/2017 | Holsten et al. |
| 2017/0238924 A1 | 8/2017 | Holsten et al. |
| 2017/0265861 A1 | 9/2017 | Holsten et al. |
| 2018/0008261 A1 | 1/2018 | Racenet et al. |
| 2018/0049739 A1 | 2/2018 | Kasvikis |
| 2018/0153544 A1 * | 6/2018 | Maddur Shankarsetty ............... A61B 90/90 |
| 2018/0221024 A1 | 8/2018 | Heinrich et al. |

FOREIGN PATENT DOCUMENTS

| | | |
|---|---|---|
| CN | 204708912 U | 10/2015 |
| CN | 107106169 A | 8/2017 |
| CN | 211484742 U | 9/2020 |
| WO | 2021051228 A1 | 3/2021 |

OTHER PUBLICATIONS

Written Opinion for Application No. PCT/CN2021/107036 dated Apr. 19, 2022.

* cited by examiner

STAPLING DEVICE WITH REPLACEABLE CARTRIDGE MODULE

FIELD

The disclosure is generally related to surgical stapling devices and, more particularly, to surgical stapling devices with replaceable cartridge modules.

BACKGROUND

Surgical stapling devices are commonly used during a variety of surgical procedures to expedite dissection and suturing of tissue while minimizing trauma to a patient. Typically, the stapling devices include an end effector that has a cartridge assembly and an anvil assembly. The cartridge assembly and the anvil assembly are movable in relation to each other between open and clamped positions to clamp tissue therebetween. When the tissue is clamped between the cartridge and anvil assemblies, the stapling device can be fired to eject staples from the cartridge assembly into a staple forming surface of the anvil assembly to suture the tissue. The stapling devices often include a knife assembly that has a cutting blade that is advanced from within the cartridge assembly into the anvil assembly to cut the tissue clamped between the cartridge and anvil assemblies.

Surgical stapling devices are available in a variety of types for performing a variety of different surgical procedures. One type of surgical stapling device includes a U-shaped end effector that has a frame having a distal transverse portion, a proximal transverse portion, and a longitudinal portion that connects the distal transverse portion to the proximal transverse portion. The proximal and distal transverse portions of the frame are spaced to define a gap. Each of the distal and proximal transverse portions has a first end coupled to the longitudinal portion and a second end spaced from the longitudinal portion. The second ends of the distal and proximal transverse portions define an opening that communicates with the gap. A clamp slide assembly has a distal portion that defines a pocket and is received within the gap in the distal portion of the frame. A cartridge module is releasably received in the pocket of the clamp slide assembly and is replaceable to facilitate reuse of the stapling device. The anvil assembly is supported on the distal transverse portion of the frame. The clamp slide assembly is movable between retracted and advanced positions to move the cartridge module into juxtaposed alignment with the anvil assembly to clamp tissue between the anvil assembly and cartridge module.

A continuing need exists in the art for an end effector that facilitates proper loading of the cartridge module into the pocket of the clamp slide assembly.

SUMMARY

This disclosure is directed to a surgical stapling device that includes a clamp slide assembly and an end effector that includes a cartridge module. The clamp slide assembly includes a distal portion that defines a curved slot and includes a linear section that defines linear channels. The cartridge module includes a curved module body that includes a linear section that has linear ribs. The linear ribs are received within the linear channels to facilitate loading of the cartridge module into the distal portion of the clamp slide assembly in a linear fashion.

Aspects of this disclosure are directed to a stapling device that includes an elongate body, a clamp slide assembly, and an end effector. The elongate body has a proximal portion and a distal portion. The clamp slide assembly has a distal portion that defines a curved pocket. The distal portion of the clamp slide assembly includes spaced walls that define a linear section of the distal portion of the clamp slide assembly. The linear section of the distal portion of the clamp slide assembly is positioned on a first end portion of the clamp slide assembly and defines linear channels. The end effector is supported on the distal portion of the elongate body and includes an end effector frame, an anvil assembly, and a cartridge module. The end effector frame has a U-shaped configuration and includes a distal transverse portion, a proximal transverse portion, and a longitudinal portion. The longitudinal portion connects the distal transverse portion to the proximal transverse portion to define a gap between the distal transverse portion and the proximal transverse portion. The distal portion of the clamp slide assembly is positioned within the gap and is movable between retracted and advanced positions. The anvil assembly is supported on the distal transverse portion of the end effector frame. The cartridge module is removably received within the curved pocket of the clamp slide assembly and includes a module body that has a curved configuration with a linear section. The linear section of the module body includes linear ribs that are received in the linear channels in the linear section of the distal portion of the clamp slide assembly when the cartridge module is loaded into the distal portion of the clamp slide assembly.

In aspects of the disclosure, each of the linear ribs of the module body includes a raised bumper.

In some aspects of the disclosure, each of the spaced side walls defining the linear section of the distal portion of the clamp slide assembly defines a pocket that communicates with one of the linear channels of the clamp slide assembly.

In certain aspects of the disclosure, the pockets receive the raised bumpers when the cartridge module is loaded into the clamp slide assembly.

In aspects of the disclosure, the spaced side walls defining the linear section of the distal portion of the clamp slide assembly define through bores that communicate with one of the pockets.

In some aspects of the disclosure, each of the raised bumpers includes indicia that are visible through the through bores in the spaced side walls of the distal portion of the clamp slide assembly when the cartridge module is loaded into the distal portion of the clamp slide assembly.

In certain aspects of the disclosure, the linear section of the cartridge module includes overhangs that define linear channels that receive portions of the spaced side walls of the distal portion of the clamp slide assembly when the cartridge module is loaded into the distal portion of the clamp slide assembly.

In aspects of the disclosure, the module body of the cartridge module includes a proximal extension, and the cartridge module includes an alignment pin assembly that is positioned within the proximal extension.

In some aspects of the disclosure, an alignment pin pusher is supported on the elongate body and has a coupling portion that engages the alignment pin assembly when the cartridge module is loaded into the distal portion of the clamp slide assembly.

In certain aspects of the disclosure, the alignment pin pusher is movable to move the alignment pin assembly between retracted and advanced positions.

In aspects of the disclosure, the proximal extension defines a cutout that facilitates passage of the coupling portion of the alignment pin pusher into the proximal extension of the module body of the cartridge module when the cartridge module is loaded into the distal portion of the clamp slide assembly.

Other aspects of the disclosure are directed to a stapling device including a handle assembly, an elongate body, a clamp slide assembly, an alignment pin pusher, and an end effector. The elongate body has a proximal portion and a distal portion. The proximal portion of the elongate body is coupled to the handle assembly. The clamp slide assembly has a distal portion that defines a curved pocket and includes spaced walls that define a linear section of the distal portion of the clamp slide assembly. The linear section of the distal portion of the clamp slide assembly is positioned on a first end portion of the clamp slide assembly and defines linear channels. The alignment pin pusher is supported on the elongate body and has a coupling portion. The end effector is supported on the distal portion of the elongate body and includes an end effector frame, an anvil assembly, and a cartridge module. The end effector frame has a U-shaped configuration and includes a distal transverse portion, a proximal transverse portion, and a longitudinal portion. The longitudinal portion connects the distal transverse portion to the proximal transverse portion to define a gap between the distal transverse portion and the proximal transverse portion. The distal portion of the clamp slide assembly is positioned within the gap and is movable between retracted and advanced positions. The anvil assembly is supported on the distal transverse portion of the end effector frame. The cartridge module is removably received within the curved pocket of the clamp slide assembly and includes a module body that has a curved configuration with a linear section. The linear section of the module body includes linear ribs that are received in the linear channels in the linear section of the distal portion of the clamp slide assembly when the cartridge module is loaded into the distal portion of the clamp slide assembly. The module body of the cartridge module includes a proximal extension. The cartridge module includes an alignment pin assembly that is positioned within the proximal extension. The coupling portion of the alignment pin pusher engages the alignment pin assembly when the cartridge module is loaded into the distal portion of the clamp slide assembly such that the alignment pin pusher is movable to move the alignment pin assembly between retracted and advanced positions.

Other aspects of the disclosure are directed to an end effector for a stapling device that includes a clamp slide assembly, an end effector frame, an anvil assembly, and a cartridge module. The clamp slide assembly has a distal portion that defines a curved pocket and includes spaced walls that define a linear section of the distal portion of the clamp slide assembly. The linear section of the distal portion of the clamp slide assembly is positioned on a first end portion of the clamp slide assembly and defines linear channels. The end effector frame has a U-shaped configuration and includes a distal transverse portion, a proximal transverse portion, and a longitudinal portion. The longitudinal portion connects the distal transverse portion to the proximal transverse portion to define a gap between the distal transverse portion and the proximal transverse portion. The distal portion of the clamp slide assembly is positioned within the gap and is movable between retracted and advanced positions. The anvil assembly is supported on the distal transverse portion of the end effector frame. The cartridge module is removably received within the curved pocket of distal portion of the clamp slide assembly and includes a module body having a curved configuration with a linear section. The linear section of the module body includes linear ribs that are received in the linear channels in the linear section of the distal portion of the clamp slide assembly when the cartridge module is loaded into the distal portion of the clamp slide assembly.

Other features of the disclosure will be appreciated from the following description.

BRIEF DESCRIPTION OF THE DRAWINGS

Various aspects of the disclosure are described herein below with reference to the drawings, wherein.

DETAILED DESCRIPTION

The disclosed surgical stapling device will now be described in detail with reference to the drawings in which like reference numerals designate identical or corresponding elements in each of the several views. However, it is to be understood that the aspects of the disclosure are merely exemplary and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. In addition, the term "clinician" is used generally to refer to medical personnel including doctors, nurses, and support personnel. Further, directional terms such as front, rear, upper, lower, top, bottom, and similar terms are used to assist in understanding the description and are not intended to limit the disclosure.

Figure 1:
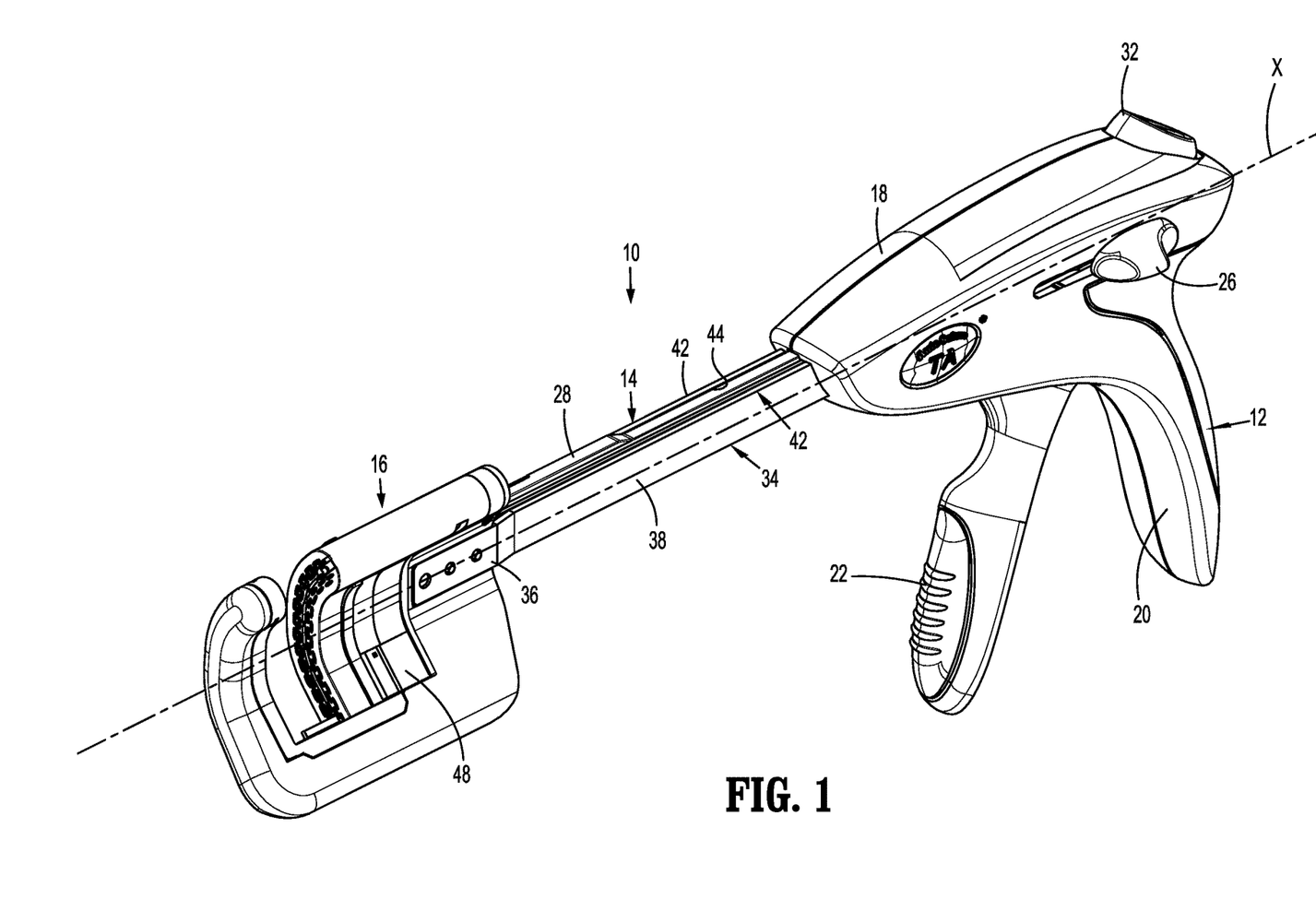
FIG. 1 is a side perspective view of a stapling device including an end effector according to aspects of the disclosure with the end effector in a pre-fired open position.

FIG. 1 illustrates the disclosed surgical stapling device shown generally as stapling device 10. The stapling device 10 includes a handle assembly 12, an elongate body 14 that extends distally from the handle assembly 12, and an end effector 16 that is supported on a distal portion of the elongate body 14. The elongate body 14 defines a longitudinal axis "X". The handle assembly 12 includes a housing 18 that defines a stationary handle 20 and supports a movable trigger 22. In aspects of the disclosure, the movable trigger 22 is supported by the housing 18 to pivot in relation to the stationary handle 20 between non-actuated and actuated positions to operate the end effector 16.

The handle assembly 12 supports knobs 26 (only one is shown) that are positioned on each side of the housing 18 and are movable along the housing 18 to advance and retract an alignment pin pusher 28. The alignment pin pusher 28 includes a coupling portion 28*a* (FIG. 2) that is positioned adjacent the end effector 16 and engages an alignment pin assembly 30 (FIG. 7) of a cartridge module 50 (FIG. 2) when the cartridge module 50 is supported on the end effector 16. The alignment pin pusher 28 is movable via the support knobs 26 to move the alignment pin assembly 30 between retracted and advanced positions. The handle assembly 12 also includes a release button 32 that can be depressed to move the end effector 16 from a clamped position to an unclamped position. For a more detailed description of a suitable handle assembly 12, see, e.g., U.S. Pat. No. 6,817, 508 ("the '508 patent").

The stapling device 10 includes a frame 34 that extends from within the handle assembly 12 to the end effector 16. The frame 34 includes a distal portion 36 that supports the end effector 16 and a proximal portion (not shown) that is supported within the housing 18 of the handle assembly 12. The frame 34 also includes a central portion 38 that includes spaced frame members 42 that define an elongate channel 44 that extends between the handle assembly 12 and the end effector 16. The elongate body 14 supports a clamp slide assembly 48 (FIG. 2), a thrust bar (not shown), and the alignment pin pusher 28, which are received within the channel 44 defined by the frame members 42 of the stapling device 10. Each of the clamp slide assembly 48, the thrust bar, and the alignment pin pusher 28 are movable between retracted and advanced positions within the channel 44 to perform the various functions of the stapling device 10, i.e., advance the alignment pin 30, move the cartridge module 50 of the end effector 16 in relation to an anvil assembly 52 of the end effector 16 between open and clamped positions, and to eject staples from the cartridge module 50.

Figure 2:
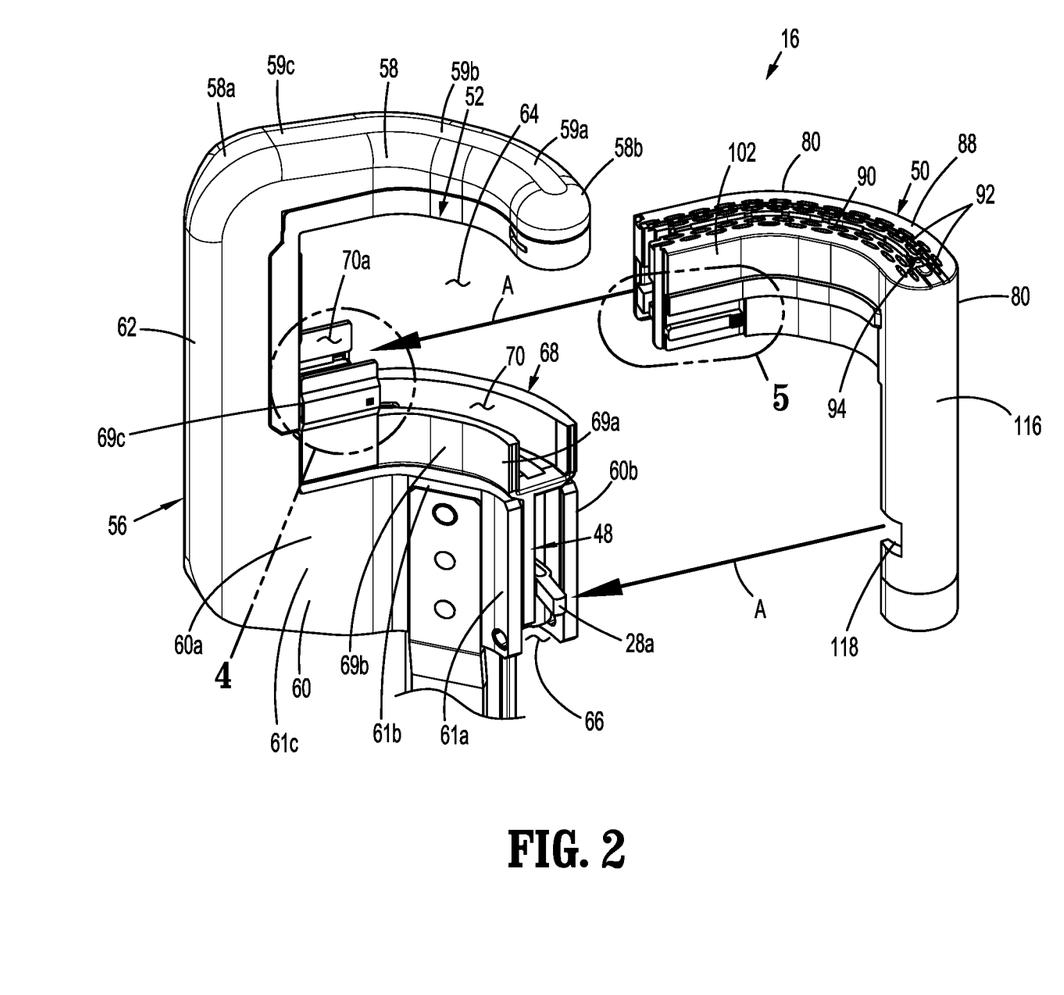
FIG. 2 is a side perspective view of the end effector of the stapling device shown in FIG. 1 with a cartridge module removed from a frame of the end effector.
Figure 3:
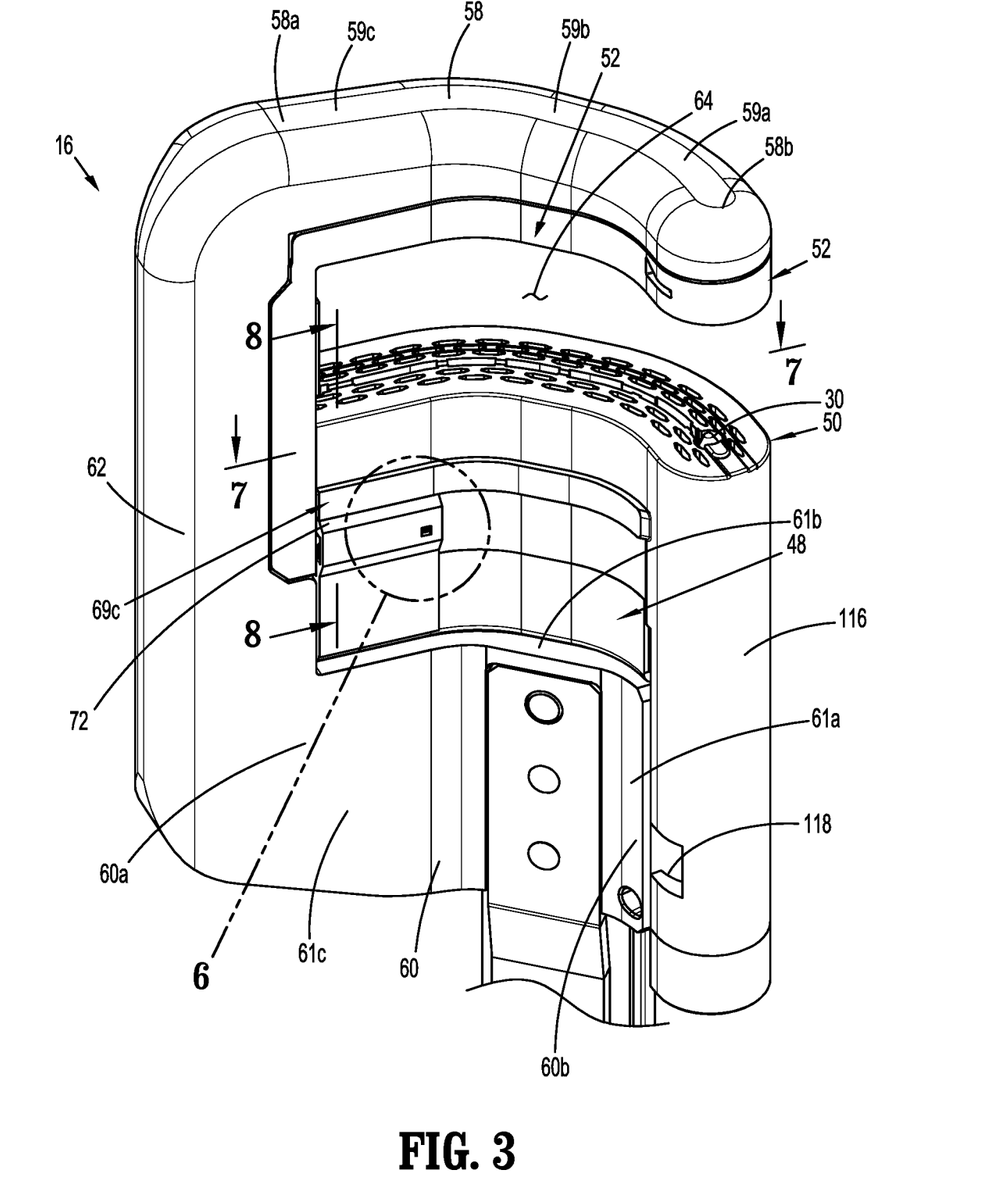
FIG. 3 is a side perspective view of the end effector shown in FIG. 2 in the pre-fired open position.

FIGS. 2 and 3 illustrate the end effector 16 of the stapling device 10 which includes an end effector frame 56 that has a U-shaped configuration and includes a distal transverse portion 58, a proximal transverse portion 60, and a longitudinal portion 62. The longitudinal portion 62 connects the distal transverse portion 58 to the proximal transverse portion 56 in spaced relation to each other to define a gap 64 that is positioned between the distal and proximal transverse portions 58, 60. In some aspects of the disclosure, the distal transverse portion 58 is formed from linear sections 59*a*, 59*b*, and 59*c* that are coupled together by radiused sections. Similarly, in aspects of the disclosure, the proximal transverse portion 60 is formed from linear sections 61*a*, 61*b*, and 61*c* that are coupled together by radiused sections.

Each of the distal and proximal transverse portions 58, 60 has a first end 58*a*, 60*a*, respectively, that is coupled to (e.g., formed with) the longitudinal portion 62 of the end effector frame 56 and a second end 58*b*, 60*b*, respectively, that is spaced from the longitudinal portion 62 of end effector frame 56. The second end 60*b* of the proximal transverse portion 60 of the end effector frame 56 is coupled to the distal portion 36 of the frame 34 of the elongate body 14 of the stapling device 10. The second end 58*b* of the distal transverse portion 58 of the end effector frame 56 is spaced from the longitudinal portion 62 such that the distal transverse portion 58 is supported on the longitudinal portion 62 in cantilevered fashion. The proximal transverse portion 60 defines a transverse slot 66 (FIG. 2) that facilitates passage of the clamp slide assembly 48 and the thrust bar (not shown) through the frame 56 into the gap 64.

The clamp slide assembly 48 includes a distal portion 68 (FIG. 2) that defines a curved pocket 70 that is configured to releasably receive cartridge module 50 (FIG. 2). The distal portion 68 of the clamp slide assembly 48 is positioned distally of the proximal transverse portion 60 of the end effector frame 56 within the gap 64 of the end effector frame 56 and has a configuration that corresponds to the configuration of the distal and proximal transverse portions 58, 60 of the end effector frame 56. More specifically, in aspects of the disclosure, the distal portion 68 of the clamp slide assembly 48 is formed from linear sections 69*a*, 69*b*, and 69*c* that are coupled together by radiused sections to define the curved pocket 70. The linear section 69*c* of the distal portion 68 of the clamp slide assembly 48 includes a pair of extended, spaced walls 72 (FIG. 4) that define a linear section 70*a* of the curved pocket 70. The linear section 70*a* of the curved pocket 70 is positioned adjacent to the longitudinal portion 62 of the end effector frame 56. The spaced walls 72 extend distally of the remaining portion of the distal portion 68 of the clamp slide assembly 48.

Figure 4:
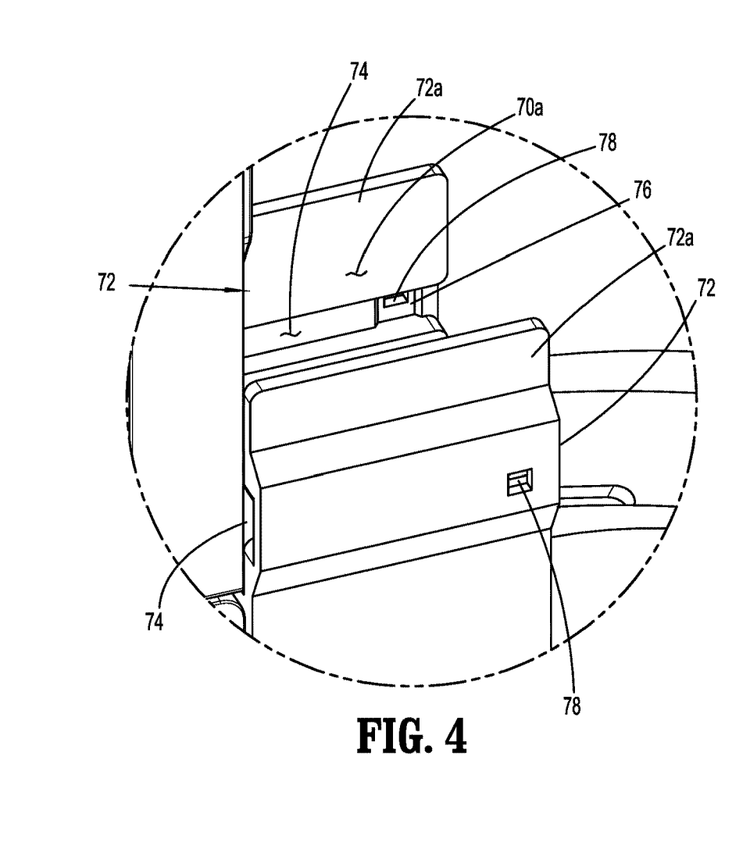
FIG. 4 is an enlarged view of the indicated area of detail shown in FIG. 2.

In aspects of the disclosure, each of the spaced walls 72 define inwardly facing linear channels 74, pockets 76, and through bores 78. The pockets 76 are formed within the linear channels 76, and the through bores 78 communicate with the pockets 76 and extend through the spaced walls 72. The clamp slide assembly 48 is movable in relation to the anvil assembly between retracted and advanced positions to move the cartridge module 50 within the gap 64 defined by the end effector frame 56 between spaced and clamped positions.

Figure 2A:
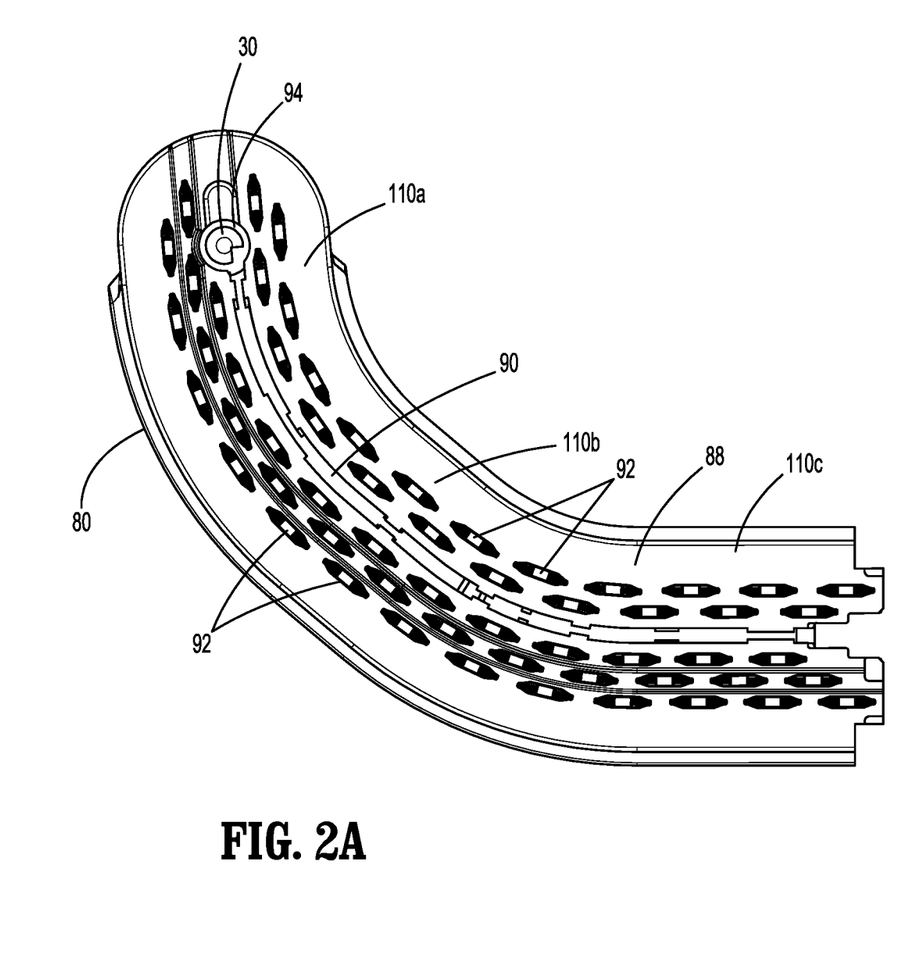
FIG. 2A is a front view of the cartridge module shown in FIG. 2.
Figure 5:
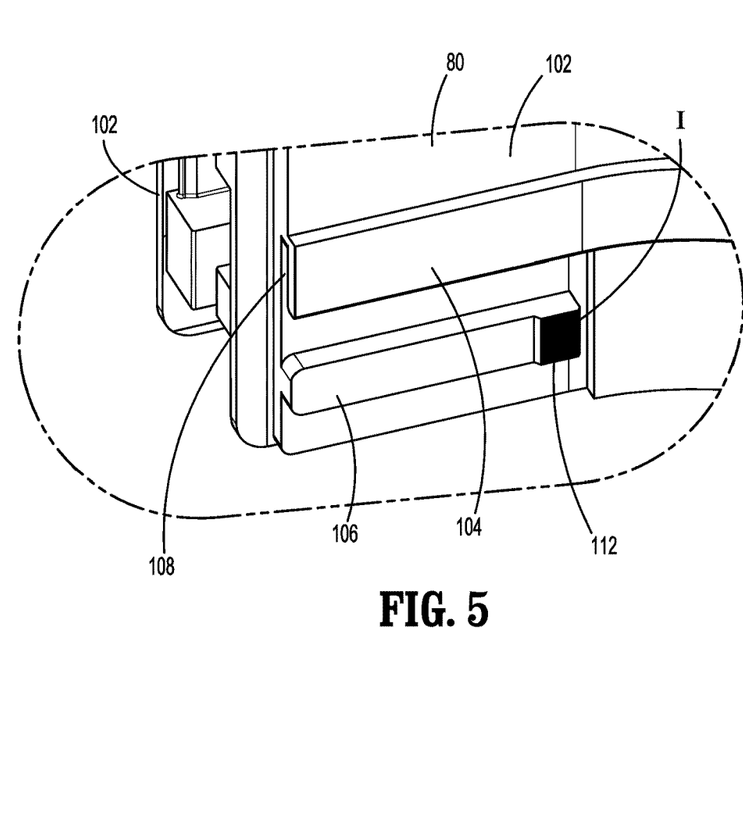
FIG. 5 is an enlarged view of the indicated area of detail shown in FIG. 2.

FIGS. 2, 2A, and 5 illustrate the cartridge module 50 which includes a module body 80, an alignment pin assembly that includes the alignment pin 30 (FIG. 2A), a knife assembly 82 (FIG. 8), a pusher 84, and staples 86. The module body 80 includes a distal surface 88 that is positioned to engage and clamp tissue against the anvil assembly 52 when the cartridge module 50 is moved to the clamped position within the gap 64 of the end effector frame 56. The module body 80 defines a knife slot 90, staple receiving slots 92 that are positioned on opposite sides of the knife slot 90, and an alignment pin bore 94 (FIG. 2A). Each of the staple receiving slots 92 receives one of the staples 86. The module body 80 defines a cavity 96 (FIG. 8) that receives the knife assembly 82 and the pusher 84 to allow movement of the knife assembly 82 and pusher 84 between retracted and advanced positions within the module body 80. The pusher 84 defines a knife slot 98 (FIG. 8) and includes fingers 84*a* that are received in the staple receiving slots 92 such that movement of the pusher 84 from its retracted position to its advanced position ejects the staples 86 from the module body 80. The knife slot 98 in the pusher 84 is aligned with the knife slot 90 in the module body 80 and receives a curved cutting blade 100 (FIG. 8) of the knife assembly 82.

The module body 80 has a configuration that corresponds to the configuration of the distal portion 68 of the clamp slide assembly 48. More specifically, the module body 80 is formed from linear sections 110*a*, 110*b*, and 110*c* (FIG. 2A) that are coupled together by radiused sections. In aspects of the disclosure, the module body 80 includes side walls 102 that define the cavity 96. Each of the side walls 102 includes an overhang 104 and a linear rib 106 that is positioned proximally of the over that overhang 104. Each of the overhangs 104 defines a channel 108 along the linear section 110c of the module body 80. The linear ribs 106 are positioned on an outer surface of the side walls 102 of the module body 80 and include raised bumpers 112 (FIG. 5). In aspects of the disclosure, the raised bumpers 112 include visual indicia "I" that are visible through the through bores 78 in the spaced side walls 72 of the distal portion 68 of the clamp slide assembly 48 when the cartridge module 80 is properly and fully received in the distal portion of the clamp slide assembly 48. In aspects of the disclosure, the indicia "I" includes a colored surface. In some aspects of the disclosure, the colored surface forming the indicia "I" includes a green colored surface although other colors and indicia are envisioned.

The module body 80 includes a proximal extension 116 (FIG. 2) that receives the alignment pin assembly 30. In aspects of the disclosure, the proximal extension 116 defines a cutout 118 that is positioned to receive the coupling portion 28a of the alignment pin pusher 28 when the module body 80 is loaded into the distal portion 68 of the clamp slide assembly 48 in a linear fashion.

Figure 6:
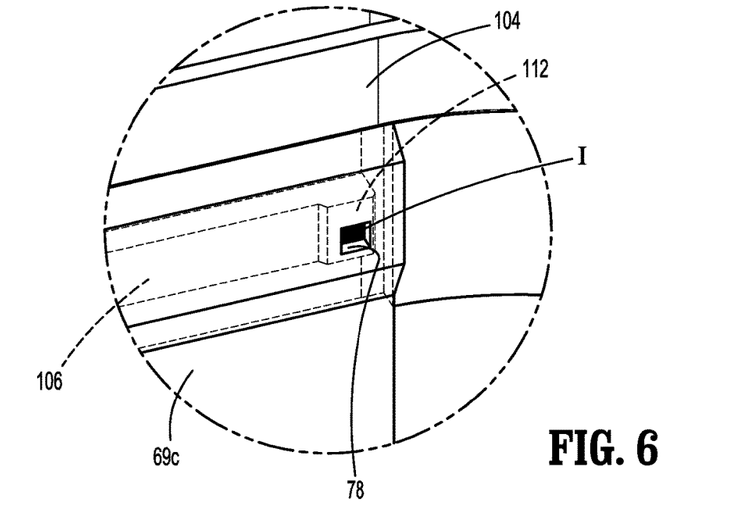
FIG. 6 is an enlarged view of the indicated area of detail shown in FIG. 3.
Figure 7:
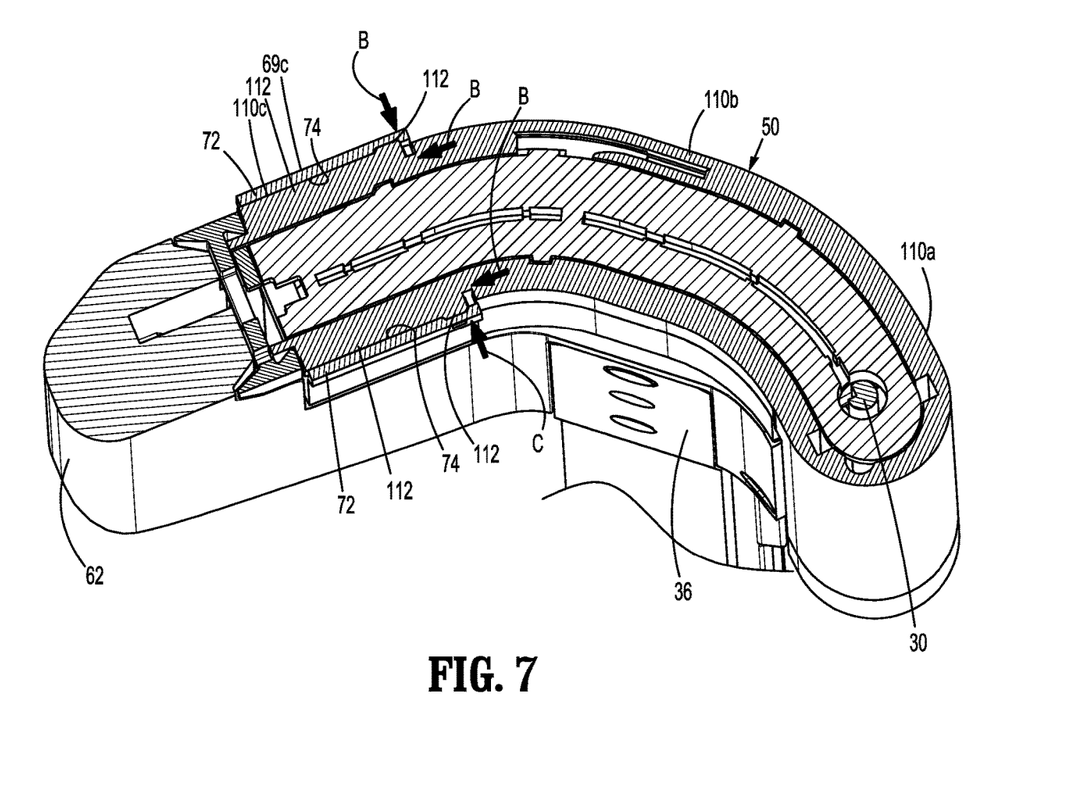
FIG. 7 is a cross-sectional view taken along section line 7-7 of FIG. 3.
Figure 8:
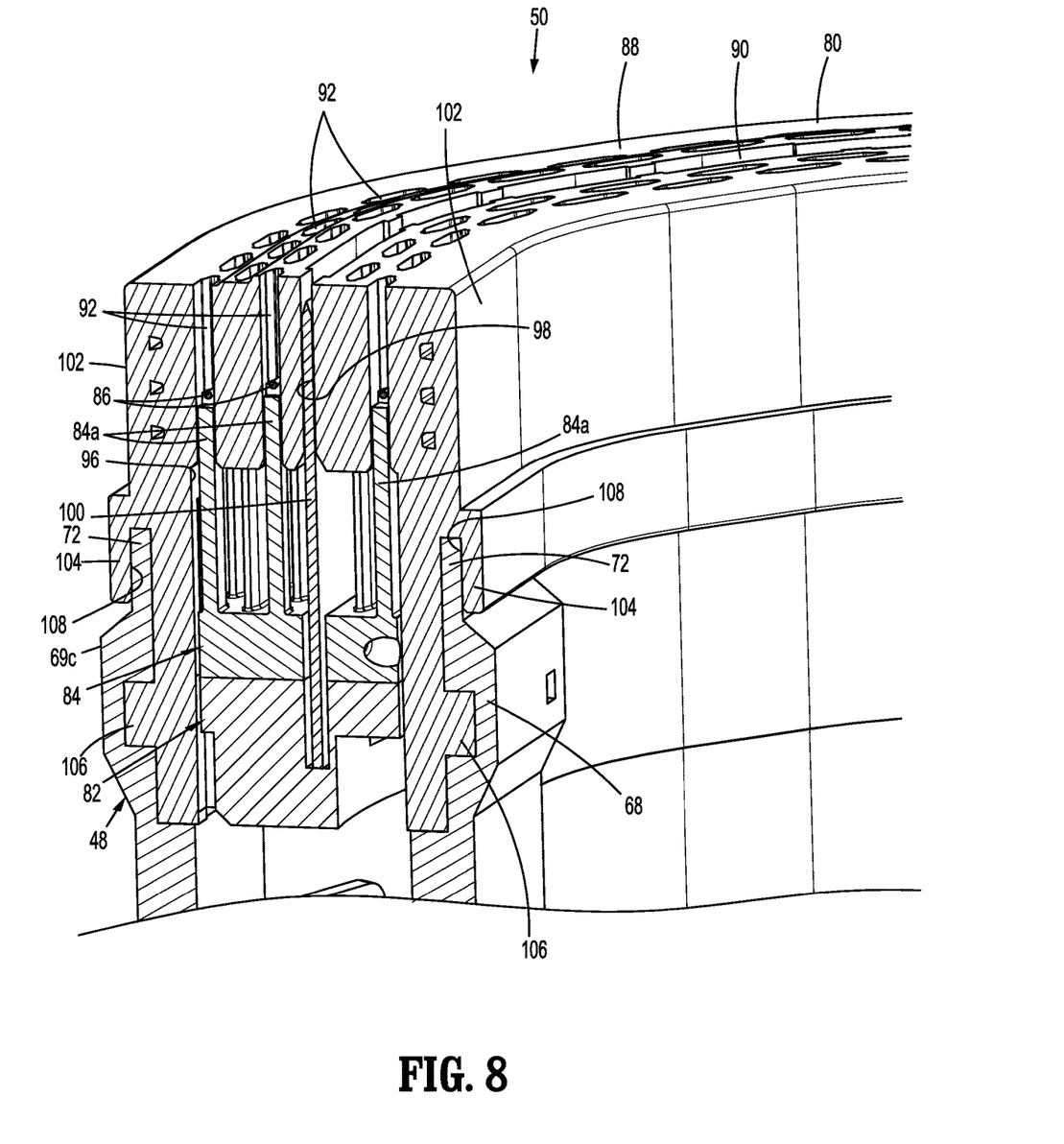
FIG. 8 is a cross-sectional view taken along section line 8-8 of FIG. 3.

FIGS. 2, 7, and 8 illustrate the end effector 16 as the cartridge module 50 is loaded into the distal portion 68 of the clamp slide assembly 48 in the direction of arrows "A" in FIG. 2. To load the cartridge module 50 into the distal portion 68 of the clamp slide assembly 48, the linear ribs 106 on the side walls 102 of the module body 80 are aligned with the linear channels 74 defined by spaced side walls 72 of the linear section 69c of the distal portion 68 of the clamp slide assembly 48. Once the linear ribs 106 are aligned with the linear channels 74, the cartridge module 50 is moved in the direction of arrows "A" in FIG. 2 to advance the linear ribs 106 into and through the linear channels 74 in the direction of arrows "B" in FIG. 7. As the cartridge module 50 is slid into the linear section 69c of the distal portion 68 of the clamp slide assembly 48, upper ends 72a (FIG. 4) of the side walls 72 are received within the channels 108 (FIG. 5) of the module body 80 of the cartridge module 50. As the linear ribs 106 move into the linear channels 74, the spaced side walls 72 of the linear section 69c of the distal portion 68 of the clamp slide assembly 48 are deformed outwardly to allow the raised bumpers 112 on linear ribs 106 to pass into the pockets 76 defined in the side walls 72 of the distal portion 68 of the clamp slide assembly 48. When the raised bumpers 112 pass into the pockets 76, the side walls 72 of the distal portion 68 of the clamp slide assembly 48 return to their non-deformed condition in the direction indicated by arrows "C" in FIG. 7 to secure the cartridge module 50 on the distal portion 68 of the clamp slide assembly 48. When the raised bumpers 112 are received in the pockets 76, the indicia "I" become visible through the through bores 78 (FIG. 6) to indicate to a clinician that the cartridge module 50 is properly and fully loaded into the clamp slide assembly 48.

When the cartridge module 50 is loaded in a linear fashion into the clamp slide assembly 48, the coupling portion 28a (FIG. 2) of the alignment pin pusher 28 (FIG. 1) passes through the cutout 118 in the proximal extension 116 of the module body 80. When the coupling portion 28a moves through the cutout 118, the coupling portion 28a engages the alignment pin assembly 30 (FIG. 7) such that longitudinal movement of the alignment pin pusher 28 causes longitudinal movement of the alignment pin assembly 30 (FIG. 7).

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A stapling device comprising:
an elongate body having a proximal portion and a distal portion;
a clamp slide assembly having a distal portion that defines a curved pocket, the distal portion of the clamp slide assembly including spaced walls that define a linear section of the distal portion of the clamp slide assembly, the linear section of the distal portion of the clamp slide assembly positioned on a first end portion of the clamp slide assembly and defining linear channels; and
an end effector supported on the distal portion of the elongate body, the end effector including:
an end effector frame having a U-shaped configuration and including a distal transverse portion, a proximal transverse portion, and a longitudinal portion, the longitudinal portion connecting the distal transverse portion to the proximal transverse portion to define a gap between the distal transverse portion and the proximal transverse portion, the distal portion of the clamp slide assembly positioned within the gap and movable between retracted and advanced positions;
an anvil assembly supported on the distal transverse portion of the end effector frame; and
a cartridge module removably received within the curved pocket of the clamp slide assembly, the cartridge module including a module body having a curved configuration with a linear section, the linear section of the module body including linear ribs that are received in the linear channels in the linear section of the distal portion of the clamp slide assembly when the cartridge module is loaded into the distal portion of the clamp slide assembly.

2. The stapling device of claim 1, wherein each of the linear ribs of the module body includes a raised bumper.

3. The stapling device of claim 2, wherein each of the spaced side walls defining the linear section of the distal portion of the clamp slide assembly defines a pocket that communicates with one of the linear channels of the clamp slide assembly, the pockets receiving the raised bumpers when the cartridge module is loaded into the clamp slide assembly.

4. The stapling device of claim 3, wherein the spaced side walls defining the linear section of the distal portion of the clamp slide assembly define through bores, each of the through bores communicating with one of the pockets.

5. The stapling device of claim 4, wherein each of the raised bumpers includes indicia, the indicia visible through the through bores in the spaced side walls of the distal portion of the clamp slide assembly when the cartridge module is loaded into the distal portion of the clamp slide assembly.

6. The stapling device of claim 5, wherein the linear section of the cartridge module includes overhangs that define linear channels, the linear channels receiving portions of the spaced side walls of the distal portion of the clamp slide assembly when the cartridge module is loaded into the distal portion of the clamp slide assembly.

7. The stapling device of claim 1, wherein the module body of the cartridge module includes a proximal extension, and the cartridge module includes an alignment pin assembly that is positioned within the proximal extension.

8. The stapling device of claim 7, further including an alignment pin pusher supported on the elongate body, the alignment pin pusher having a coupling portion that engages the alignment pin assembly when the cartridge module is loaded into the distal portion of the clamp slide assembly, wherein the alignment pin pusher is movable to move the alignment pin assembly between retracted and advanced positions.

9. The stapling device of claim 8, wherein the proximal extension defines a cutout, the cutout facilitating passage of the coupling portion of the alignment pin pusher into the proximal extension of the module body of the cartridge module.

10. A stapling device comprising:
a handle assembly;
an elongate body having a proximal portion and a distal portion, the proximal portion of the elongate body coupled to the handle assembly;
a clamp slide assembly having a distal portion that defines a curved pocket, the distal portion of the clamp slide assembly including spaced walls that define a linear section of the distal portion of the clamp slide assembly, the linear section of the distal portion of the clamp slide assembly positioned on a first end portion of the clamp slide assembly and defining linear channels;
an alignment pin pusher supported on the elongate body, the alignment pin pusher having a coupling portion; and
an end effector supported on the distal portion of the elongate body, the end effector including:
an end effector frame having a U-shaped configuration and including a distal transverse portion, a proximal transverse portion, and a longitudinal portion, the longitudinal portion connecting the distal transverse portion to the proximal transverse portion to define a gap between the distal transverse portion and the proximal transverse portion, the distal portion of the clamp slide assembly positioned within the gap and movable between retracted and advanced positions;
an anvil assembly supported on the distal transverse portion of the end effector frame;
a cartridge module removably received within the curved pocket of the clamp slide assembly, the cartridge module including a module body having a curved configuration with a linear section, the linear section of the module body including linear ribs that are received in the linear channels in the linear section of the distal portion of the clamp slide assembly when the cartridge module is loaded into the distal portion of the clamp slide assembly, the module body of the cartridge module including a proximal extension, the cartridge module including an alignment pin assembly that is positioned within the proximal extension, wherein the coupling portion of the alignment pin pusher engages the alignment pin assembly when the cartridge module is loaded into the distal portion of the clamp slide assembly such that the alignment pin pusher is movable to move the alignment pin assembly between retracted and advanced positions.

11. The stapling device of claim 10, wherein the proximal extension defines a cutout, the cutout facilitating passage of the coupling portion of the alignment pin pusher into the proximal extension of the module body of the cartridge module when the cartridge module is loaded into the distal portion of the clamp slide assembly.

12. The stapling device of claim 10, wherein each of the linear ribs of the module body includes a raised bumper.

13. The stapling device of claim 12, wherein each of the spaced side walls defining the linear section of the distal portion of the clamp slide assembly defines a pocket that communicates with one of the linear channels of the clamp slide assembly, the pockets receiving the raised bumpers when the cartridge module is loaded into the clamp slide assembly.

14. The stapling device of claim 13, wherein each of the raised bumpers includes indicia, the indicia visible through the through bores in the spaced side walls of the distal portion of the clamp slide assembly when the cartridge module is loaded into the distal portion of the clamp slide assembly.

15. The stapling device of claim 14, wherein the linear section of the cartridge module includes overhangs that define linear channels, the linear channels receiving portions of the spaced side walls of the distal portion of the clamp slide assembly when the cartridge module is loaded into the distal portion of the clamp slide assembly.

16. An end effector for a stapling device comprising:
a clamp slide assembly having a distal portion that defines a curved pocket, the distal portion of the clamp slide assembly including spaced walls that define a linear section of the distal portion of the clamp slide assembly, the linear section of the distal portion of the clamp slide assembly positioned on a first end portion of the clamp slide assembly and defining linear channels;
an end effector frame having a U-shaped configuration and including a distal transverse portion, a proximal transverse portion, and a longitudinal portion, the longitudinal portion connecting the distal transverse portion to the proximal transverse portion to define a gap between the distal transverse portion and the proximal transverse portion, the distal portion of the clamp slide assembly positioned within the gap and movable between retracted and advanced positions;
an anvil assembly supported on the distal transverse portion of the end effector frame;
a cartridge module removably received within the curved pocket of distal portion of the clamp slide assembly, the cartridge module including a module body having a curved configuration with a linear section, the linear section of the module body including linear ribs that are received in the linear channels in the linear section of the distal portion of the clamp slide assembly when the cartridge module is loaded into the distal portion of the clamp slide assembly.

17. The end effector of claim 16, wherein the linear section of the distal portion of the clamp slide assembly is positioned adjacent the longitudinal portion of the end effector frame.

18. The end effector of claim 17, wherein each of the linear ribs of the module body includes a raised bumper.

19. The end effector of claim 18, wherein each of the spaced side walls defining the linear section of the distal portion of the clamp slide assembly defines a pocket that communicates with one of the linear channels of the clamp slide assembly, the pockets receiving the raised bumpers when the cartridge module is loaded into the clamp slide assembly.

20. The end effector of claim 19, wherein the spaced side walls defining the linear section of the distal portion of the clamp slide assembly define through bores, each of the through bores communicating with one of the pockets, each of the raised bumpers having indicia that is visible through the through bores in the spaced side walls of the distal portion of the clamp slide assembly when the cartridge module is loaded into the distal portion of the clamp slide assembly.

* * * * *